United States Patent
Syvret et al.

(10) Patent No.: US 10,562,831 B2
(45) Date of Patent: Feb. 18, 2020

(54) PROCESS FOR MAKING TETRACHLOROPROPENE BY CATALYZED GAS-PHASE DEHYDROCHLORINATION OF PENTACHLOROPROPANE

(71) Applicant: Arkema Inc., King of Prussia, PA (US)

(72) Inventors: Robert G. Syvret, Allentown, PA (US); Daniel Alford, Jr., King of Prussia, PA (US); Anne Pigamo, Francheville (FR)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 15/761,137

(22) PCT Filed: Sep. 15, 2016

(86) PCT No.: PCT/US2016/051822
§ 371 (c)(1),
(2) Date: Mar. 19, 2018

(87) PCT Pub. No.: WO2017/053159
PCT Pub. Date: Mar. 30, 2017

(65) Prior Publication Data
US 2018/0265435 A1 Sep. 20, 2018

Related U.S. Application Data

(60) Provisional application No. 62/221,250, filed on Sep. 21, 2015.

(51) Int. Cl.
*C07C 17/25* (2006.01)
*C07C 21/04* (2006.01)

(52) U.S. Cl.
CPC .............. *C07C 17/25* (2013.01); *C07C 21/04* (2013.01); *C07C 2523/26* (2013.01); *C07C 2523/755* (2013.01); *C07C 2527/12* (2013.01)

(58) Field of Classification Search
CPC ......... C07C 17/25; C07C 21/21; C07C 21/24; C07C 17/23; C07C 2526/755; C07C 2527/12

See application file for complete search history.

(56) References Cited

U.S. PATENT DOCUMENTS

| | | |
|---|---|---|
| 3,049,567 A | 8/1962 | Frantz |
| 3,497,565 A | 2/1970 | Legendre |
| 5,689,020 A | 11/1997 | Boyce |
| 5,811,603 A | 9/1998 | Elsheikh |
| 7,094,936 B1 | 8/2006 | Owens et al. |
| 7,670,477 B2 | 3/2010 | Louret et al. |
| 8,304,589 B2 | 11/2012 | Fukuju et al. |
| 8,895,788 B2 | 11/2014 | Elsheikh et al. |
| 8,907,147 B2 | 12/2014 | Wang et al. |
| 2003/0028057 A1 | 2/2003 | Owens et al. |
| 2003/0116474 A1 | 6/2003 | Towler et al. |
| 2011/0083955 A1 | 4/2011 | Tirtowidjojo et al. |
| 2011/0087055 A1 | 4/2011 | Tirtowidjojo et al. |
| 2011/0196178 A1 | 8/2011 | Nyberg |
| 2011/0218369 A1 | 9/2011 | Elsheikh et al. |
| 2012/0048776 A1 | 3/2012 | Podrebarac et al. |
| 2012/0078020 A1 | 3/2012 | Elsheikh et al. |
| 2012/0103013 A1 | 5/2012 | King et al. |
| 2012/0190902 A1 | 7/2012 | Nyberg |
| 2012/0289751 A1 | 11/2012 | Nose et al. |
| 2013/0211155 A1 | 8/2013 | Nair et al. |
| 2014/0081055 A1 | 3/2014 | Tirtowidjojo et al. |
| 2014/0100394 A1 | 4/2014 | Dakka et al. |
| 2017/0308036 A1 | 10/2017 | Kitamura et al. |

FOREIGN PATENT DOCUMENTS

| | | |
|---|---|---|
| FR | 1496124 | 5/1966 |
| GB | 1181873 | 2/1970 |
| GB | 1 268 842 | 3/1972 |
| WO | WO 2013/074324 A1 * | 5/2013 |

* cited by examiner

*Primary Examiner* — Jafar F Parsa
(74) *Attorney, Agent, or Firm* — Steven D. Boyd

(57) ABSTRACT

The present disclosure relates to catalyzed gas-phase dehydrochlorination of a pentachloropropane to form a tetrachloropropene with high selectivity and purity.

19 Claims, 1 Drawing Sheet

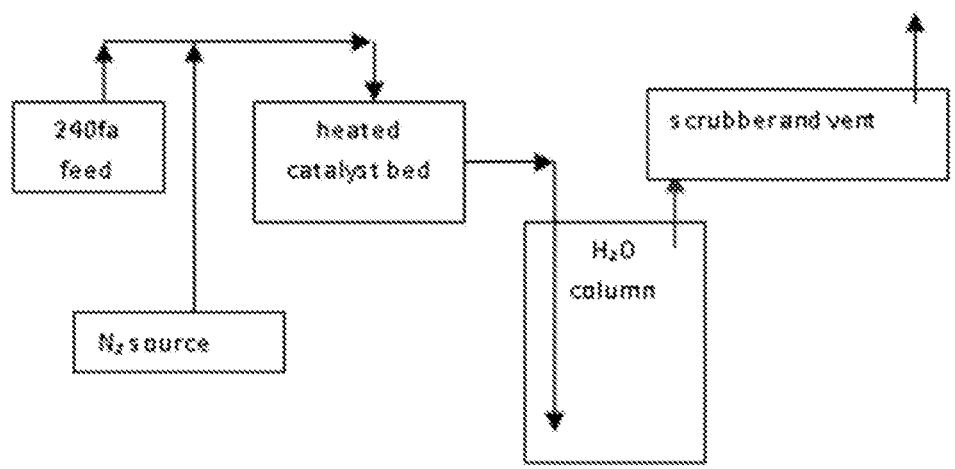

US 10,562,831 B2

PROCESS FOR MAKING TETRACHLOROPROPENE BY CATALYZED GAS-PHASE DEHYDROCHLORINATION OF PENTACHLOROPROPANE

This present application is the national phase under 35 USC § 371 of prior PCT International Application Number PCT/US2016/051822 filed Sep. 15, 2016 which designated the United States of America and claimed priority to U.S. Provisional Patent Application Ser. No. 62/221,250 filed Sep. 21, 2015.

FIELD OF THE INVENTION

This invention relates to gas-phase dehydrochlorination of a pentachloropropane to make a tetrachloropropene.

BACKGROUND OF THE INVENTION

Numerous methods have been disclosed for the preparation of tetrachloropropenes, including 1,1,3,3-tetrachloroprop-1-ene (1230za). These methods vary widely in both starting materials, reaction conditions, and selectivity.

U.S. Patent Application Publication Nos. 2011/0083955 and 2011/0087055 disclose methods for preparation of 1230za through the reaction of methylene chloride and trichloroethylene. These methods produce 1230za with up to 94% selectivity.

U.S. Patent Application Publication No. 2013/0211155 discloses a method for preparing 1230za by a dechlorination reaction with Zn metal of $CCl_3CHClCHCl_2$ (230 da) in a $CH_3OH$ solvent with formation of 1230za in 70% yield.

U.S. Pat. No. 5,689,020 discloses a high temperature chlorination process in which mixtures of propene and/or chlorinated propenes diluted in $CCl_4$ or $N_2$ are chlorinated with $Cl_2$ to provide mixtures of 1230za and 1,3,3,3-tetrachloropropene (1230zd).

U.S. Patent Application Publication Nos. 2012/0190902 and 2011/0196178 disclose methods for stabilizing tetrachloropropenes using antioxidants.

U.S. Pat. No. 7,094,936 discloses a method for producing 1230za by reaction of $CCl_4$ with vinyl chloride. Liquid phase dechlorination of 1,1,1,3,3-pentachloropropane (240fa) to form 1230za is also disclosed.

U.S. Pat. No. 3,497,565 discloses a process for production of chloropropenes by chlorination of chloropropenylsulfides with $Cl_2$.

French Patent No. FR 1.496.124 and British Patent No. GB 1,181,873 disclose a process for chlorination of alkenyl thioesters to produce a mixture of 1230za and 1230zd. A method for converting 1230zd to 1230za is also disclosed.

U.S. Pat. No. 8,304,589 discloses a method for production of 240fa from $CCl_4$ and vinyl chloride. A process for thermolysis of 240fa to 1230za at a temperature of 500° C. is also disclosed.

There is a need for a method of producing tetrachloropropenes with high selectivity and purity that is scalable up for commercial manufacturing.

SUMMARY OF THE INVENTION

The present invention relates to the catalyzed gas-phase dehydrochlorination of a pentachloropropane to form a tetrachloropropene.

A first aspect of the present invention relates to a process for preparing a tetrachloropropene, comprising flowing a gaseous pentachloropropane over a catalyst at a temperature less than 500° C. to form a tetrachloropropene.

A further aspect of the present invention relates to a process for preparing 1,1,3,3-tetrachloropropene (1230za) comprising flowing 1,1,1,3,3-pentachloropropane (240fa) over a catalyst at a temperature of less than 500° C. at a contact time of 0.5 to 120 seconds to produce 1,1,3,3-tetrachloropropene.

BRIEF DESCRIPTION OF THE DRAWING

The FIGURE shows a flow diagram of the dehydrochlorination process according to an embodiment of the present invention.

DETAILED DESCRIPTION OF THE INVENTION

The present invention relates to the catalyzed gas-phase dehydrochlorination of a pentachloropropane to form a tetrachloropropene.

According to at least one embodiment of the present invention, 1,1,1,3,3-pentachloropropane (240fa) is dehydrochlorinated to prepare 1,1,3,3-tetrachloropropene according to the reaction of Formula (1).

$$CCl_3CH_2CHCl_2 \xrightarrow[\Delta]{\text{catalyst}} Cl_2C=CHCHCl_2 + HCl \quad (1)$$
$$\quad\text{240fa} \qquad\qquad\qquad \text{1230za}$$

In at least one embodiment, 1,1,1,2,3-pentachloropropane (240db) is dehydrochlorinated to prepare 1,1,2,3-tetrachloroprop-1-ene (1230xa) according to the reaction of Formula (2).

$$CCl_3CHClCH_2Cl \xrightarrow[\Delta]{\text{catalyst}} Cl_2C=CClCH_2Cl + HCl \quad (2)$$
$$\quad\text{240db} \qquad\qquad\qquad \text{1230xa}$$

The FIGURE shows a schematic diagram to illustrate the dehydrochlorination reaction in accordance with an embodiment of the present invention. In the FIGURE, a feed gas containing 240fa is diluted with nitrogen. The diluted feed gas is flowed over a heated catalyst bed. The effluent from the catalyst bed can be passed through a water column to collect the any unreacted 240fa and the 1230za product, along with any soluble products, such as HCl. The effluent from the water column can then be passed through a caustic scrubber and vented to the atmosphere.

According to at least one embodiment, the pentachloropropane flows over a catalyst at a temperature less than 500° C. In at least one embodiment, the temperature of the catalyst ranges from about 200° C. to about 450° C., such as, for example, from about 200° C. to about 350° C. According to at least one embodiment, the dehydrochlorination takes place at a temperature of about 250° C.

At high temperatures, there is a risk that catalyst deactivation can occur more rapidly since decomposition and subsequent coking is more likely to occur on the catalyst surface at higher temperatures. Additionally, at temperatures above 500° C., it is expected that pentachloropropanes will thermally decompose. At lower temperatures, the reaction proceeds more slowly, which may decrease the efficiency of the process.

According to at least one embodiment, the catalyst may be chosen from metal catalysts, transition metal oxides, and dehydrochlorination catalysts known in the art. Examples of transition metal oxides that may be used include, but are not limited to, nickel oxide, chromium oxides ($Cr_2O_3$, $CrO_3$), zirconium oxide, and magnesium oxide. In accordance with at least one embodiment, the catalyst may be chosen from metal catalysts, aluminum fluoride, and combinations thereof. The metal catalyst may be chosen from, for example, nickel, chromium and combinations thereof. In at least one embodiment, the catalyst comprises nickel/chromium. In at least one other embodiment, the catalyst comprises aluminum fluoride. In other embodiments, the catalyst comprises nickel/chromium supported by aluminum fluoride.

In at least one embodiment, the catalyst may be activated. For example, the catalyst may be pre-fluorinated. According to at least one embodiment, the catalyst may be pre-fluorinated by contacting the catalyst with hydrofluoric acid.

The contact time between the pentachloropropane and catalyst may vary. In at least one embodiment, the contact time between the pentachloropropane and catalyst ranges from about 1 second to about 120 seconds, such as, for example, from about 20 seconds to about 80 seconds, or from about 30 seconds to about 60 seconds.

In at least one embodiment, the contact time may be shorter and a recycling loop may be used to return unreacted pentachloropropane to the catalyst.

In accordance with at least one embodiment, the pentachloropropane is diluted with an inert gas, such as, for example, nitrogen. The molar ratio of the inert gas to the pentachloropropane can be varied based on the flow rate of the pentachloropropane, the contact time between the pentachloropropane and the catalyst, etc. The molar ratio of the inert gas to the pentachloropropane can range from 0, where no inert gas is employed, to about 5. In an alternate embodiment, the molar ratio of the inert gas to the pentachloropropane can range from about 1 to about 3.

Aspects of the present invention include:

1. A process for preparing a tetrachloropropene, comprising:
    flowing a gaseous pentachloropropane over a catalyst at a temperature less than 500° C. to form a tetrachloropropene.
2. The process of claim 1, wherein the pentachloropropane is 1,1,1,3,3-pentachloropropane (240fa) and the tetrachloropropene is 1,1,3,3-tetrachloropropene.
3. The process of claim 1, wherein the pentachloropropane is 1,1,1,2,3-pentachloropropane and the tetrachloropropene is 1,1,2,3-tetrachloroprop-1-ene.
4. The process of any of the previous claims, wherein the catalyst is selected from transition metal oxides, metal catalysts, aluminum fluoride, and combinations thereof.
5. The process of any of the previous claims, wherein the metal catalyst is selected from nickel, chromium, and combinations thereof.
6. The process of any of the previous claims, wherein the catalyst is a pre-fluorinated catalyst.
7. The process of any of the previous claims, further comprising activating the catalyst by pre-fluorinating the catalyst.
8. The process of any of the previous claims, wherein pre-fluorinating the catalyst comprises contacting the catalyst with hydrofluoric acid.
9. The process of any of the previous claims, wherein catalyst is at a temperature ranging from about 200° C. to about 450° C.
10. The process of any of the previous claims, wherein the catalyst is at a temperature ranging from about 200° C. to about 350° C.
11. The process of any of the previous claims, wherein the tetrachloropropene is captured in a water column.
12. The process of any of the previous claims, wherein the pentachloropropane is in contact with the catalyst for a contact time of 1 to 120 seconds.
13. The process of any of the previous claims, wherein the pentachloropropane is in contact with the catalyst for a contact time of 20 to 80 seconds.
14. The process of any of the previous claims, further comprising diluting the pentachloropropane in an inert gas.
15. A process for preparing 1,1,3,3-tetrachloropropene (1230za) comprising:
    flowing 1,1,1,3,3-pentachloropropane (240fa) over a catalyst at a temperature of less than 500° C. at a contact time of 1 to 120 seconds to produce 1,1,3,3-tetrachloropropene.
16. The process of claim 15, wherein the catalyst is selected from transition metal oxides, metal catalysts, aluminum fluoride, and combinations thereof.
17. The process of any of claims 15 and 16, wherein the contact time ranges from 20 to 80 seconds.
18. The process of claims any of 15 through 17, wherein the catalyst comprises nickel/chromium supported on aluminum fluoride.
19. The process of any of claims 15 through 18, wherein the catalyst is pre-fluorinated.
20. The process of any of claims 15 through 19, wherein the catalyst is at a temperature of 200° C. to 350° C.

Within this specification embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein The following examples illustrate the present invention and are not intended to limit the scope thereof.

EXPERIMENTAL PROCEDURE

The following is a general procedure for evaluating different catalysts. A catalyst is loaded into the catalyst bed (the catalyst is fixed between 2 layers of $Al_2O_3$ support material) and heated to the desired temperature. The pentachloropropane and optional inert gas are flowed through the catalyst bed at a rate to provide the desired contact time on the catalyst bed (for example, from 1 to 60 seconds) and for a desired duration (for example, 24 hours). The pentachloropropane and inert gas may be provided using pumps and/or mass flow controllers to control the flow of gas through the catalyst bed. Following the desired time duration, the flow of pentachloropropane and optional inert gas is stopped. The water column is weighed prior to manipulation and then the organic (non-aqueous) and aqueous layers are phase separated. Each phase is weighed and analyzed. The aqueous and non-aqueous phases can separately be analyzed for organics including unreacted pentachloropropane and the tetrachloropropene product as well as for soluble chlorine species including HCl. The non-aqueous phase components, in particular the pentachloropropane and the tetrachloropropene, are analyzed by $^1$H NMR spectroscopy and/or GC-MS.

Example 1: Dehydrochlorination of 240Fa Over an Activated Ni/Cr Supported on AlF$_3$ Catalyst An activated Ni/Cr supported on AlF$_3$ catalyst (1/16" to 1/8" bead form) was loaded into the catalyst bed (1" o.d. Hastelloy pipe). The term "activated" means the catalyst was pre-fluorinated with HF prior to use. The bed was heated to 250° C. The water column was loaded with 500.47 g of fresh de-ionized H$_2$O. A flow of 240fa (1,1,1,3,3-pentachloropropane) was initiated and was delivered to the catalyst bed at the rate of 2.3 g/h (4 cc/min) as a mixture with N$_2$ which was delivered at 8 cc/min. Thus, the molar ratio of N$_2$ to 240fa in this experiment was 2:1. The effluent from the reactor was directed through the H$_2$O column. The flow of 240fa/N$_2$ was continued for 24 hours during which time a total of 56 g of 240fa was delivered to the catalyst bed. After the specified time, the flow of 240fa was stopped and the N$_2$ flow was continued to ensure that all labile organic materials have been purged from the catalyst bed. Next, the water column was removed and the contents weighed (549.09 g). The resulting two phases were separated and individually weighed. The aqueous phase weighed 514 g. The organic phase weighed 35.09 g. Analysis of the organic phase by $^1$H NMR indicated 99% selectivity to 1,1,3,3-tetrachloroprop-1-ene (1230za) and 1% selectivity to 240fa. Thus, in this experiment, the recovery was 549.09/556.47=98.7% and the selectivity to 1230za was 99%.

Part "B" of this experiment was accomplished as follows: A fresh load of de-ionized H$_2$O (500.13 g) was loaded into the H$_2$O column and the flow of 240fa/N$_2$ resumed for an additional 24 hours. Following this, the products were isolated, weighed and analyzed as described above. This experiment was run a total of 11 consecutive times (Experiments 1A-K) and the results are summarized in Table 1.

TABLE 1

| Ex. | Catalyst | T (° C.) | contact time (sec) | Expt. duration (hours) | 240fa delivered | fresh H$_2$O mass (g) | recovered H$_2$O mass (g) | organic mass recovered (g) | % recovery | Selectivity to 1230za by $^1$H NMR (%) |
|---|---|---|---|---|---|---|---|---|---|---|
| 1A | activated[1] Ni/Cr on AlF$_3$ | 250 | 60 | 24 | 56 | 500.47 | 514 | 35.09 | 98.7 | 99 |
| 1B | activated[1] Ni/Cr on AlF$_3$ | 250 | 60 | 24 | 58.5 | 500.13 | 511.04 | 38.62 | 98.4 | 99 |
| 1C | activated[1] Ni/Cr on AlF$_3$ | 250 | 60 | 24 | 62 | 500.12 | 509.98 | 33.7 | 96.7 | 99 |
| 1D | activated[1] Ni/Cr on AlF$_3$ | 250 | 60 | 25 | 65 | 500.06 | 512.01 | 49.53 | 99.4 | 99 |
| 1E | activated[1] Ni/Cr on AlF$_3$ | 250 | 60 | 24 | 58.5 | 499.9 | 510.26 | 46.29 | 99.7 | 99 |
| 1F | activated[1] Ni/Cr on AlF$_3$ | 250 | 60 | 24 | 63 | 500.22 | 511.84 | 50.96 | 99.9 | 98 |
| 1G | activated[1] Ni/Cr on AlF$_3$ | 250 | 60 | 24 | 51 | 500.51 | 510.18 | 33.75 | 98.6 | 99 |
| 1H | activated[1] Ni/Cr on AlF$_3$ | 250 | 60 | 24 | 65 | 501.92 | 512.44 | 48.74 | 99.0 | 94 |
| (1I)[2] | activated[1] Ni/Cr on AlF$_3$ | 250 | 60 | 24 | 54 | 500.52 | 509.69 | 33.83 | 98.0 | 95 |
| 1J | activated[1] Ni/Cr on AlF$_3$ | 250 | 30 | 24 | 119.5 | 501.12 | 516.46 | 95.46 | 98.6 | 78 |
| 1K | activated[1] Ni/Cr on AlF$_3$ | 250 | 60 | 26 | 66 | 500.73 | 510.46 | 44.1 | 97.9 | 84 |

[1]Activated means the Ni/Cr on AlF$_3$ was pre-fluorinated with HF prior to use.
[2]Between Experiments 1I and 1J the catalyst bed was cooled to ambient temperature and N$_2$ flowed through for 35 days

Example 2: Dehydrochlorination of 240Fa Over a Non-Activated Ni/Cr Supported on AlF$_3$ Catalyst A non-activated Ni/Cr supported on AlF$_3$ catalyst (1/16" to 1/8" bead form) was loaded into the catalyst bed (1" o.d. Hastelloy pipe). The term "non-activated" means the catalyst was not pre-fluorinated with HF prior to use. The procedure described in Example 1 was repeated in this example and the parameters and results are summarized in Table 2.

TABLE 2

| Ex. # | Catalyst | Temp (° C.) | contact time (sec) | Expt. duration (hours) | 240fa delivered | fresh $H_2O$ mass (g) | recovered $H_2O$ mass (g) | organic mass recovered (g) | % recovery | Selectivity to 1230za by $^1H$ NMR (%) |
|---|---|---|---|---|---|---|---|---|---|---|
| 2A | non-activated[1] Ni/Cr on AlF$_3$ | 250 | 60 | 11 (24) | 30.5 | 501.3 | 508.92 | 7.65 | 97.1 | 95 |
| 2B | non-activated[1] Ni/Cr on AlF$_3$ | 250 | 60 | 24 | 60 | 500.68 | 513.59 | 44.7 | 99.6 | >99.5 |
| 2C | non-activated[1] Ni/Cr on AlF$_3$ | 250 | 60 | 24 | 61.5 | 500.19 | 509.56 | 38.44 | 97.6 | 100 |
| 2D | non-activated[1] Ni/Cr on AlF$_3$ | 250 | 60 | 24 | 61 | 502.67 | 513.87 | 47.66 | 99.6 | 99.5 |
| 2E | non-activated[1] Ni/Cr on AlF$_3$ | 250 | 60 | 24 | 61 | 500.66 | 511.3 | 46.94 | 99 | 97.5 |

[1]Non-activated means the Ni/Cr on AlF$_3$ was not pre-fluorinated with HF prior to use.

Example 3: Dehydrochlorination of 240Fa Over a Ni/Cr Supported on AlF$_3$ Fluorination Catalyst A Ni/Cr supported on AlF$_3$ catalyst (1/16" to 1/8" bead form) that was used previously for catalysis of the gas-phase fluorination reaction between anhydrous HF and 240fa yielding mixtures of Z-1233zd (cis) and E-1233zd (trans) was evaluated in the catalyst bed by an experimental procedure similar to that described in Example 1. The parameters and results are summarized in Table 3.

TABLE 3

| Ex. # | Catalyst | Temp (° C.) | contact time (sec) | Expt. duration (hours) | 240fa delivered | fresh $H_2O$ mass (g) | recovered $H_2O$ mass (g) | organic mass recovered (g) | % recovery | Selectivity to 1230za by $^1H$ NMR (%) |
|---|---|---|---|---|---|---|---|---|---|---|
| (3A)[1] | Ni/Cr on AlF$_3$ | 250 | 10 | 24 | 256.5 | not used | not used | 150.07 | 58.5 | 97 |
| 3B | Ni/Cr on AlF$_3$ | 250 | 10 | 24 | 317.5 | 503 | 523.78 | 285.6 | 98.6 | 32 |
| 3C | Ni/Cr on AlF$_3$ | 300 | 10 | 24 | 331 | 504 | Not Recorded | 298.08 | | 34 |
| 3D | Ni/Cr on AlF$_3$ | 300 | 60 | 28 | 97 | 501 | 513.42 | 76.35 | 98.6 | 50 |

[1]A water column was not used in Experiment 3A. The organic product was collected at ambient temperature in the vessel used as the $H_2O$ column, but without containing $H_2O$ Example 4: Comparative. Dehydrochlorination of 240Fa Over AlF$_3$ Neat AlF$_3$ in 1/16" bead form was loaded into the catalyst bed (1" o.d. Hastelloy pipe). The procedure described in Example 1 was repeated in this example and the parameters and results are summarized in Table 4.

This comparative example demonstrates that AlF$_3$ is quickly de-activated during dehydrochlorination experiments and that the activity can be partially regained by regeneration of the bed with air. The air regeneration presumably removes deposited organics thus rendering the bed more active for dehydrochlorination.

TABLE 4

| Ex. # | Catalyst | Temp (° C.) | contact time (sec) | Expt. duration (hours) | 240fa delivered | fresh $H_2O$ mass (g) | recovered $H_2O$ mass (g) | organic mass recovered (g) | % recovery | Selectivity to 1230za by $^1H$ NMR (%) |
|---|---|---|---|---|---|---|---|---|---|---|
| 4A | neat $AlF_3$ | 300 | 60 | 24 | 49.5 | 501.62 | 516.26 | 27.72 | 98.7 | 100 |
| 4B | neat $AlF_3$ | 300 | 30 | 24 | 111 | 500.73 | 520.94 | 77.12 | 97.8 | 93 |
| 4C | neat $AlF_3$ | 300 | 45 | 24 | 74.5 | 500.18 | 508.87 | 51.94 | 97.6 | 55 |
| (4D)[1] | neat $AlF_3$ | 300 | 60 | 25 | 57.5 | 508.26 | 513.32 | 49.89 | 99.5 | 32 |
| (4E)[1] | neat $AlF_3$ | 300 | 60 | 22 | 47.5 | 500.58 | 510.34 | 26.81 | 98.0 | 79 |
| (4F)[2] | neat $AlF_3$ | 300 | 60 | 18 | 31 | 500.33 | 505.67 | 29.74 | 100.8 | 54 |
| (4G)[2] | neat $AlF_3$ | 250 | 60 | 22 | 59.5 | 500.24 | 509.56 | 35.58 | 97.4 | 82 |
| 4H | neat $AlF_3$ | 250 | 60 | 46 | 112 | 500.11 | 509.28 | 98.35 | 99.3 | 40 |
| 4I | neat $AlF_3$ | 250 | 60 | 24 | 57 | 500.01 | 504.7 | 46.65 | 99.0 | 32 |

[1]Between Experiments 4D and 4E the $AlF_3$ catalyst bed was treated with air at 300 over a weekend. This was an attempt to "de-coke" and re-activate the catalyst.
[2]Between Experiments 4F and 4G the $AlF_3$ catalyst bed was treated with air at 300 over a weekend. This was an attempt to "de-coke" and re-activate the catalyst.

Example 5: Comparative. Dehydrochlorination of 240Fa with BASF HCl Adsorbent CL750

A commercial HCl adsorbent (BASF CL-760 in 1/16" bead form) was loaded into the catalyst bed (1" o.d. Hastelloy pipe). The procedure described in Example 1 was repeated in this example and the parameters and results are summarized in Table 5.

This comparative example demonstrates that although a commercial material is useful as an adsorbent for HCl, it is not necessarily useful for catalytic dehydrochlorination. In this particular example, the results clearly show that the bed becomes increasingly deactivated, probably due to irreversible adsorption on the surface of the material.

TABLE 5

| Ex. # | Catalyst | Temp (° C.) | contact time (sec) | Expt. duration (hours) | 240fa delivered | fresh $H_2O$ mass (g) | recovered $H_2O$ mass (g) | organic mass recovered (g) | % recovery | Selectivity to 1230za by $^1H$ NMR (%) |
|---|---|---|---|---|---|---|---|---|---|---|
| (5A)[1] | BASF CL-760 | 250 | 60 | 24 | 61 | 507.31 | 524.58 | 20.79 | 96.0 | 71 |
| 5B | BASF CL-760 | 250 | 60 | 24 | 60.5 | 503.88 | 506.73 | 42.66 | 97.3 | 15 |
| 5C | BASF CL-760 | 250 | 60 | 24 | 61.5 | 500.71 | 502.56 | 60.38 | 100.1 | 10 |

[1]A 10° C. exotherm was observed during Experiment 5A and was presumably due to adsorption of HCl on the bed of CL-760.

Example 6: Comparative. Dehydrochlorination of 240Fa with a 0.5% Pd/C Catalyst

A commercial source of 0.5% Pd on C in 1/16" bead form was loaded into the catalyst bed (1" o.d. Hastelloy pipe). The procedure described in Example 1 was repeated in this example and the parameters and results are summarized in Table 6.

This comparative example demonstrates that 0.5% Pd/C, a material sometimes useful for dehydrochlorination, is not always effective for dehydrochlorination. In this particular example, it was not effective at all.

TABLE 6

| Ex. # | Catalyst | Temp (° C.) | contact time (sec) | Expt. duration (hours) | 240fa delivered | fresh H$_2$O mass (g) | recovered H$_2$O mass (g) | organic mass recovered (g) | % recovery | Selectivity to 1230za by $^1$H NMR (%) |
|---|---|---|---|---|---|---|---|---|---|---|
| 6 | 0.5% Pd on C | 300 | 60 | 23 | 57 | 501.69 | 512.19 | 25.66 | 96.3 | very low |

Example 7: Comparative. Dehydrochlorination of 240Fa Over Al$_2$O$_3$

Neat Al$_2$O$_3$ in 1/16" bead form was loaded into the catalyst bed (1" o.d. Hastelloy pipe). The procedure described in Example 1 was repeated in this example and the parameters and results are summarized in Table 7.

This comparative example demonstrates that Al$_2$O$_3$ which is used as the catalyst support in all of the previous examples is not active for dehydrochlorination of 240fa.

| Ex. # | Catalyst | Temp (° C.) | contact time (sec) | Expt. duration (hours) | 240fa delivered | fresh H$_2$O mass (g) | recovered H$_2$O mass (g) | organic mass recovered (g) | % recovery | Selectivity to 1230za by $^1$H NMR (%) |
|---|---|---|---|---|---|---|---|---|---|---|
| 7A | Al$_2$O$_3$ | 250 | 60 | 23 | 59.5 | 506.96 | 508.66 | 41.25 | 97.1 | 2.4 |
| 7B | Al$_2$O$_3$ | 250 | 60 | 21 | 52 | 508.15 | 509.68 | 53.08 | 100.5 | 2.0 |

Example 8: Dehydrochlorination of 240db Over a Non-Activated Ni/Cr Supported on AlF$_3$ Catalyst to Give 1230Xa In a manner similar to that described in Example 2, dehydrochlorination of 1,1,1,2,3-pentachloropropane (240db) to 1,1,2,3-tetrachloroprop-1-ene (1230xa) is accomplished by passing 240db through the catalyst bed with a sufficient contact time and at the appropriate temperature to accomplish the desired conversion.

A non-activated Ni/Cr supported on AlF$_3$ catalyst (1/16" to 1/8" bead form) was loaded into the catalyst bed (1" o.d. Hastelloy pipe). The term "non-activated" means the catalyst was not pre-fluorinated with HF prior to use. The bed was heated to 250° C. The water column was loaded with 500.19 g of fresh de-ionized H$_2$O. A flow of 240db (1,1,1,2,3-pentachloropropane) was initiated and was delivered to the catalyst bed at the rate of 2.52 g/h (4 7 cc/min) as a mixture with N$_2$ which was delivered at 8 cc/min. Thus, the molar ratio of N$_2$ to 240db in this experiment was 1.7:1. The effluent from the reactor was directed through the H$_2$O column. The flow of 240db/N$_2$ was continued for 24 hours during which time a total of 60.5 g of 240db was delivered to the catalyst bed. After the specified time, the flow of 240db was stopped and the N$_2$ flow was continued to ensure that all labile organic materials have been purged from the catalyst bed. Next, the water column was removed and the contents weighed (550.23 g). The resulting two phases were separated and individually weighed. The aqueous phase weighed 512.98 g. The organic phase weighed 37.25 g. Analysis of the organic phase by $^1$H NMR indicated 100% selectivity to 1,1,2,3-tetrachloroprop-1-ene (1230xa) and 0% selectivity to 240db. Thus, in this experiment, the recovery was 550.23/560.69=98.1% and the selectivity to 1230xa was 100%.

Part "B" of this experiment was accomplished as follows: A fresh load of de-ionized H$_2$O (501.42 g) was loaded into the H$_2$O column and the flow of 240db/N$_2$ resumed for an additional 7 hours. Following this, the products were isolated, weighed and analyzed as described above. In this experiment there was a 99% recovery of products with 100% selectivity to the desired 1230xa.

The experiment with 240db to 1230xa was run twice (Ex. 8A-B) and the results are summarized in Table 8.

| Ex. # | Catalyst | Temp (° C.) | contact time (sec) | Expt. duration (hours) | 240db delivered | fresh H$_2$O mass (g) | recovered H$_2$O mass (g) | organic mass recovered (g) | % recovery | Selectivity to 1230xa by $^1$H NMR (%) |
|---|---|---|---|---|---|---|---|---|---|---|
| 8A | non-activated[1] Ni/Cr on AlF$_3$ | 250 | 60 | 24 | 60.5 | 500.19 | 512.98 | 37.25 | 98.1 | 100 |
| 8B | non-activated[1] Ni/Cr on AlF$_3$ | 250 | 60 | 7 | 19 | 501.42 | 505 | 10.18 | 99.0 | 100 |

[1]Non-activated means the Ni/Cr on AlF$_3$ was not pre-fluorinated with HF prior to use.

The invention claimed is:

1. A process for preparing a tetrachloropropene, comprising:
   flowing a gaseous combination comprising pentachloropropane and an inert gas consisting of nitrogen, over a catalyst at a temperature less than 500° C. to form a tetrachloropropene.

2. The process of claim 1, wherein the pentachloropropane is 1,1,1,3,3-pentachloropropane (240fa) and the tetrachloropropene is 1,1,3,3-tetrachloropropene.

3. The process of claim 1, wherein the pentachloropropane is 1,1,1,2,3-pentachloropropane and the tetrachloropropene is 1,1,2,3-tetrachloroprop-1-ene.

4. The process of claim 1, wherein the catalyst is selected from transition metal oxides, metal catalysts, aluminum fluoride, and combinations thereof.

5. The process of claim 4, wherein the metal catalyst is selected from nickel, chromium, and combinations thereof.

6. The process of claim 4, wherein the catalyst is a pre-fluorinated catalyst.

7. The process of claim 1, further comprising activating the catalyst by pre-fluorinating the catalyst.

8. The process of claim 7, wherein pre-fluorinating the catalyst comprises contacting the catalyst with hydrofluoric acid.

9. The process of claim 1, wherein catalyst is at a temperature ranging from about 200° C. to about 450° C.

10. The process of claim 9, wherein the catalyst is at a temperature ranging from about 200° C. to about 350° C.

11. The process of claim 1, wherein the tetrachloropropene is captured in a water column.

12. The process of claim 1, wherein the pentachloropropane is in contact with the catalyst for a contact time of 1 to 120 seconds.

13. The process of claim 12, wherein the pentachloropropane is in contact with the catalyst for a contact time of 20 to 80 seconds.

14. A process for preparing 1,1,3,3-tetrachloropropene (1230za) comprising:
   Flowing gaseous combination comprising 1,1,1,3,3-pentachloropropane (240fa) and an inert gas consisting of nitrogen over a catalyst at a temperature of less than 500° C. at a contact time of 1 to 120 seconds to produce 1,1,3,3-tetrachloropropene.

15. The process of claim 14, wherein the catalyst is selected from transition metal oxides, metal catalysts, aluminum fluoride, and combinations thereof.

16. The process of claim 14, wherein the contact time ranges from 20 to 80 seconds.

17. The process of claim 14, wherein the catalyst comprises nickel/chromium supported on aluminum fluoride.

18. The process of claim 14, wherein the catalyst is pre-fluorinated.

19. The process of claim 14, wherein the catalyst is at a temperature of 200° C. to 350° C.

* * * * *